US00PP33937P2

(12) United States Plant Patent
Randag

(10) Patent No.: US PP33,937 P2
(45) Date of Patent: Feb. 1, 2022

(54) CALLA LILY PLANT NAMED 'DOZANSUNY'

(50) Latin Name: *Zantedeschia sprengeri*
Varietal Denomination: Dozansuny

(71) Applicant: Dümmen Group B.V., De Lier (NL)

(72) Inventor: Cecilius Jan-Jochem Randag, Koedijk (NL)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 17/307,250

(22) Filed: May 4, 2021

(51) Int. Cl.
*A01H 5/02* (2018.01)
*A01H 6/10* (2018.01)

(52) U.S. Cl.
USPC ..... Plt./490

(58) Field of Classification Search
USPC ..... Plt./490
CPC ... A01H 5/02; A01H 5/00; A01H 6/10; A01H 6/56
See application file for complete search history.

(56) References Cited

U.S. PATENT DOCUMENTS

PP29,119 P3 * 3/2018 Randag ..... Plt./490

OTHER PUBLICATIONS

CS Weijers, retrieved on Aug. 2, 2021, retrieved from the Internet at https://www.csweijers.nl/assortiment/zantedeschia, 11 pp. (Year: 2021).*

Visions Pictures, retrieved on Aug. 2, 2021, retrieved from the Internet at https://www.visionspictures.com/en/asset/420782_zantedeschia-sunya, one page. (Year: 2021).*

* cited by examiner

*Primary Examiner* — June Hwu
(74) *Attorney, Agent, or Firm* — The Webb Law Firm

(57) ABSTRACT

'Dozansuny' is a new variety of calla lily plant having yellow colored spathes that produces 4-7 inflorescences per 16-18 cm tuber. The flower stems are about 25-34.5 cm in height. The leaves are dark green with maculations present and a smooth texture.

2 Drawing Sheets

Botanical classification: *Zantedeschia sprengeri*.
Varietal denomination: 'Dozansuny'.

BACKGROUND OF THE NEW PLANT

The present invention comprises a new and distinct variety of calla lily, botanically known as *Zantedeschia sprengeri* and hereinafter referred to by the varietal name 'Dozansuny'. 'Dozansuny' is a product of a planned breeding program, which had the objective of creating *Zantedeschia* hybrids for pot flower production in a wide range of colors with a classic flower shape. The new cultivar is a seedling selected from the crossing of *Zantedeschia sprengeri* seedling Z041943-887 (female parent, unpatented) with *Zantedeschia sprengeri* variety 'Fursa' (male parent, U.S. Plant Pat. No. 29,119). 'Dozansuny' was selected in 2014 by the inventor in 't Zand, The Netherlands as one flowering plant within the progeny of the stated cross.

The first act of asexual reproduction of 'Dozansuny' by tissue culture was performed by the inventor in November of 2014 in 't Zand, The Netherlands. Subsequent asexual reproductions by tissue culture at the same location have demonstrated that the combination of characteristics as herein disclosed for the new cultivar are retained and reproduced true to type through successive generations of asexual reproduction.

The following observations, measurements and comparisons describe plants at approximately 9 weeks from planting in 14 cm pots in 't Zand, The Netherlands under greenhouse conditions, which approximate those generally used in horticultural practice. Color references are made to The 2001 R.H.S. Colour Chart of The Royal Horticultural Society of London, 4$^{th}$ Edition, except where general color terms of ordinary significance are used.

The present invention has not been evaluated under all possible environmental conditions. The phenotype may vary with variations in environment without a change in the genotype of the plant.

The following traits have been repeatedly observed and determined to be basic characteristics of 'Dozansuny' which, in combination, distinguish this calla lily as a new and distinct cultivar:

1. Medium yellow colored spathes without a throat spot;
2. Dark green colored leaves; and
3. Few leaf maculations present.

The new variety is similar to its female parent. in the following traits: spathe, spadix, and stein color, leaf shape, and the presence of leaf maculations. However, 'Dozansuny' exhibits a broader spathe width, longer spathe and spadix length, and more leaf maculations than its female parent. Further, its female parent has a spathe throat spot. The new variety is similar to its male parent in the following traits: spathe and stern color, leaf shape, and the presence of leaf maculations. However, 'Dozansuny' exhibits a broader spathe width, longer spathe and spadix length, weaker flower curve, and fewer leaf maculations than its male parent. Further, its male parent has a spathe throat spot and a yellow orange colored spadix.

When compared to calla lily plant named 'Yellow Jacket BLZ' (U.S. Plant Pat. No. 20,217), the upper surface spathe color is similar, but the lower surface spathe color of 'Yellow Jacket BLZ' is Yellow Group RHS 7B.

BRIEF DESCRIPTION OF THE DRAWINGS

The accompanying photographic drawings illustrate the new variety taken at approximately 10 and 9 weeks of aac, respectively, with the colors being as nearly true as is possible with color illustrations of this type.

DESCRIPTION OF THE NEW PLANT

Figure 1:
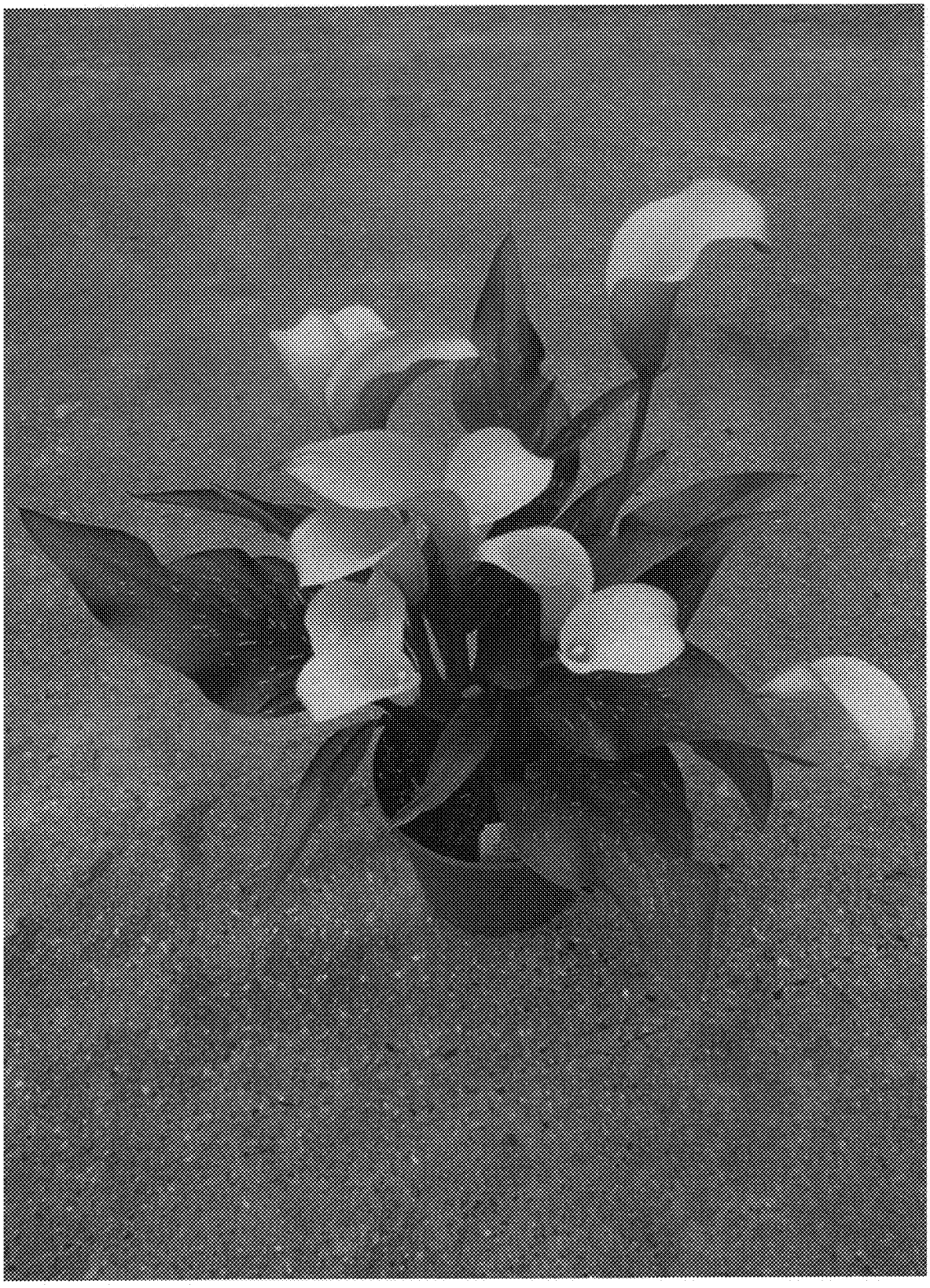
FIG. 1 illustrates a single flowering plant of the new variety.
Figure 2:
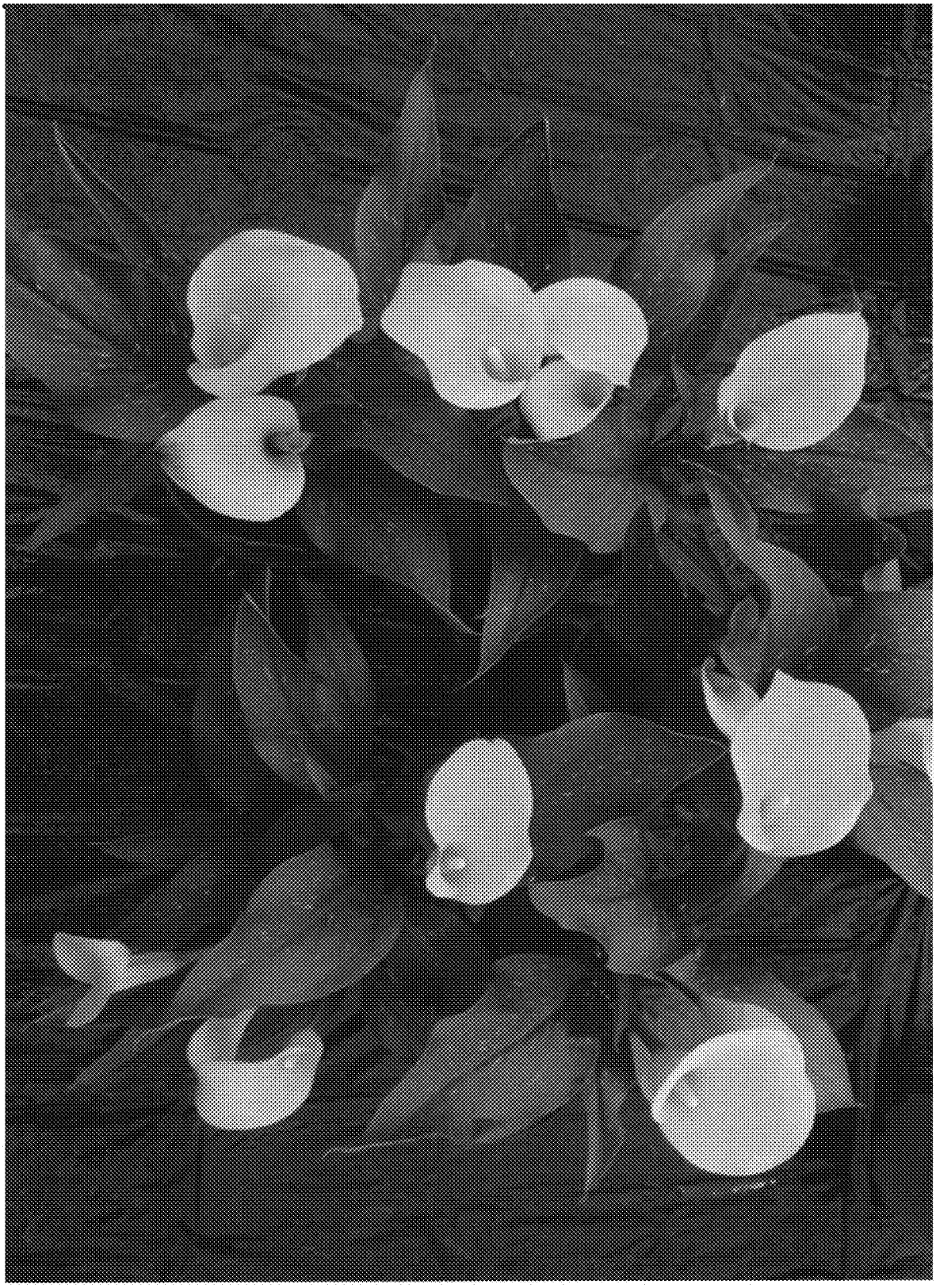
FIG. 2 illustrates multiple flowering plants of the new variety.

Type: Deciduous.

Size:

*Height of the leaf canopy above the soil.*—29-35 cm.

*Height of top of inflorescences above the soil.*—25-34.5 cm.

*Diameter.*—27-41 cm.

Form: Semi-spreading.

Number of inflorescences per tuber:

*Size* 16-18 cm in diameter.—4-7 inflorescences.

Branches:

*Number.*—Average.

*Color.*—Yellow-Green Group RHS 149B to 149C.

*Young shoot color.*—Yellow-Green Group RHS 151B to 151C.

Leaves:

*Size.*—Width: 7-9 cm, with the broadest part being in the middle. Length: 11.5-20.5 cm.

*Number per plant.*—12-21.

*Leaf blade lobes.*—Absent.

*Shape.*—Elliptic.

*Apex.*—Apiculate.

*Base.*—Attenuate.

*Margin.*—Entire; having a color of Yellow-Green Group RHS 144B to 144C.

*Color.*—Upper surface: Yellow-Green Group RHS 147A, with few, linear Greyed-White Group RHS 156C to 156D maculations present. Lower surface: Yellow-Green Group RHS 147B, with few, linear Green-White Group RHS 157C maculations present.

*Veins.*—Configuration: Pinnate. Color: Yellow-Green Group RHS 146C to 146D.

*Surface texture.*—Smooth (both surfaces).

*Petiole.*—Length: 11.5-14 cm. Diameter: 4-7 mm. Color: The base and upper part are Yellow-Green Group RHS 144A to 144B.

Roots:

*Color.*—White Group RHS 155C.

*Branching description.*—Fibrous root system. Several main roots emerge from the top of the tuber and form a small number of lateral roots.

Spathe:

*Size.*—Length (measured from opening to tip): 4.5-7 cm. Width: 3-6 cm. Height: 7-9 cm.

*Color* (*at all stages of maturity and fading*).—Throat spot: Absent. Upper surface: Yellow Group RHS 7A. Lower surface: Yellow-Green Group RHS 149B to 149C.

*Vein color.*—Green-Yellow Group RHS 1C.

*Shape.*—Funnel.

*Apex.*—Apiculate.

*Base.*—Attenuate.

*Margin.*—Entire with weak rectifying and a color of Yellow Group RHS 7A.

Spadix:

*Shape.*—Cylinder.

*Size.*—Length: 30-45 mm. Diameter: 7-17 mm.

*Color.*—Yellow Group RHS 9A to 13A.

*Position relative to spathe.*—Upright.

Peduncle:

*Size.*—Length: 18.5-24 cm. Diameter: 10-12 mm.

*Color.*—The upper part is Yellow-Green Group RHS 144B to 144C, the lower part is Yellow-Green Group RHS 144A.

*Texture.*—Smooth.

Reproductive organs:

*Location of female organs.*—Basal position of the spadix.

*Location of male organs.*—Upper position of the spadix.

*Perianth.*—Conspicuous.

*Stamens.*—Presence: Not visible before pollen release. Number: Between 480 and 600. Pollen amount: Scarce. Color: Between White Group RHS 155B and 155C.

*Anther.*—Shape: Round. Length: Less than 1 mm. Color: Yellow Group RHS 8B to 8C.

*Filament.*—Length: Less than 1 mm. Color: White Group RHS 155D.

*Pistils.*—Number: 15 to 30. Length beyond perianth: About 1 mm.

*Stigma.*—Shape: Round. Size: Less than 1 mm.

*Style.*—Length: Less than 1 mm. Color: Yellow Group RHS 8B to 8C.

*Ovaries.*—Texture: Smooth. Length: Between 1 to 10 mm. Width: Between 1 to 10 mm. Color: The top color is Yellow Group RHS 13A, the bottom color is Yellow Group RHS 3C to 3D.

Seeds:

*Length.*—2.5-3.8 mm.

*Width.*—2.1-2.6 mm.

*Color.*—Brown Group RHS 200A to 200B.

*Amount.*—29 per inflorescence.

Disease resistance: No unusual susceptibility/resistance to diseases noticed to date.

Pest resistance: No unusual susceptibility/resistance to pests noticed to date.

Heat tolerance: No heat tolerance.

Hardiness: Not tested to date.

Flowering: in general, the time from indoor and outdoor planting to first flowering takes about eight weeks in The Netherlands.

Lastingness: About two weeks on the plant.

Fragrance: None.

I claim:

1. A new and distinct variety of calla lily plant named 'Dozansuny' as herein described and illustrated.

* * * * *